(12) United States Patent
Eijsink et al.

(10) Patent No.: US 6,790,951 B1
(45) Date of Patent: Sep. 14, 2004

(54) EXPRESSION SYSTEM IN MICROORGANISM AND ITS USE FOR EXPRESSING HETEROLOGOUS AND HOMOLOGOUS PROTEINS

(76) Inventors: Vincent G. H. Eijsink, Måltrostveien 52B, N-1430 Ås (NO); Ingolf F. Nes, Bjørkeveien 3, N-1430 Ås (NO); May B. Brurberg, Måltrostveien 52B, N-1430 Ås (NO)

( * ) Notice: Subject to any disclaimer, the term of this patent is extended or adjusted under 35 U.S.C. 154(b) by 0 days.

(21) Appl. No.: 09/068,507

(22) PCT Filed: Nov. 13, 1996

(86) PCT No.: PCT/NO96/00266

§ 371 (c)(1),
(2), (4) Date: Jul. 15, 1998

(87) PCT Pub. No.: WO97/18316

PCT Pub. Date: May 22, 1997

(30) Foreign Application Priority Data

Nov. 13, 1995 (NO) ................................................ 954575

(51) Int. Cl.⁷ .......................... C07H 21/04; C12N 1/21; C12N 15/74; C07K 7/08; C07K 14/95
(52) U.S. Cl. .................. 536/24.1; 536/23.1; 435/252.3; 435/320.1; 530/324; 530/326
(58) Field of Search ............................... 536/24.1, 23.1, 536/23.7, 23.2; 435/252.3, 320.1, 69.1; 530/324, 326; 485/69.1, 252.3, 320.1

(56) References Cited

U.S. PATENT DOCUMENTS 5,914,248 A * 6/1999 Kuipers et al. ............ 435/69.1

FOREIGN PATENT DOCUMENTS

| EP | 0493779 A1 | 7/1992 |
| WO | 119802 A1 | 12/1991 |
| WO | 9404682 A1 | 3/1994 |

OTHER PUBLICATIONS

Huhne et al. (1996) Microbiology, vol. 142, pp. 1437–1448.*
Dzung Bao Diep et al., *Molecular Microbiology*, vol. 18, No. 4, pp. 631–639 (1995).
Petra S. Tichaczek, *Microbiology* vol. 140, pp. 361–367, (1994).
Koen Venema et al., *Molecular Microbiology*, vol. 17, No. 39, pp. 515–522, fig. 1 and summary (1995).
Dzung Bao Diep et al., *Applied Environmental Microbiology*, vol. 60, No. 1, pp. 160–166 (1994).
Lars Axelsson et al., *Journal of Bacteriology*, vol. 177, No. 8, pp. 2125–2137 (1995).
Marco J. van Belkum et al., *Applied and Environmental Microbiology*, vol. 57, No. 2, pp. 492–498, fig. 1 (1991).
Naomi Balaban et al., *Proc. Natl. Acad. Sci. USA*, vol. 92, pp. 1619–1623 (1995).
*Chemical Abstracts*, vol. 121, No. 4725e, (1994).
Askild L. Holck et al., *FEMS Microbiology Letters*, vol. 115, (1994), pp. 143–150.
John S. Parkinson et al., *Cell*, vol. 73, (Jun. 4, 1993), pp. 857–871.
Frank D. Russo et al., *Trends In Microbiology*, vol. 1, No. 8, (Nov. 1993), pp. 306–310.
Jeffry B. Stock et al., *Microbiological Reviews*, vol. 53, No. 4, (Dec. 1989), pp. 450–490.
Petra S. Tichaczek et al., *System Appl. Microbiol.*, vol. 15, (1992), pp. 460–468.
A.L. Holck et al., GENBANK Accession No. z48542 [gi:695615]—Dec. 18, 1996.
Lars Axelsson et al., Applied Environmental Microbiology, vol. 59, No. 9, (Sep. 1993).

* cited by examiner

*Primary Examiner*—Elizabeth Slobodyansky
(74) *Attorney, Agent, or Firm*—Birch, Stewart, Kolasch & Birch, LLP

(57) ABSTRACT

The present invention concerns the discovery of a new regulatory mechanism for gene expression in lactic acid bacteria (LAB), especially *Lactobacillus sake* LTH673 or *Lactobacillus plantarium* C11, that includes previously unrecognized strongly regulable promoter elements. The essential finding is that the expression of genes under the control of a promoter element dependent on the expression of the IF-K-R gene cluster. The expression of the IF-K-R gene cluster is autoinduced by the secreted peptide encoded by IF, thus providing a regulable expression system for a desired protein. The invention further comprises the purified IF protein.

28 Claims, 3 Drawing Sheets

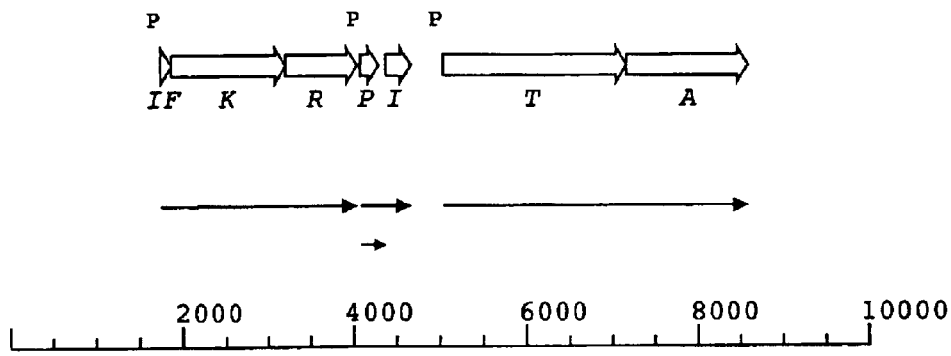

Fig. 1

```
atgatgatatttaaaaaactttcagaaaaagaattgcaaaaaataaacggtggtatggcagga
 M  M  I  F  K  K  L  S  E  K  E  L  Q  K  I  N  G  G  M  A  G aatagttctaattttattcataagattaaacaaattttttacccatcgttaa
 N  S  S  N  F  I  H  K  I  K  Q  I  F  T  H  R  *
```

Fig. 2

```
atggaaaagtttattgaattatctttaaaagaagtaacagcaattacaggtggaaaatattat
 M  E  K  F  I  E  L  S  L  K  E  V  T  A  I  T  G  G  K  Y  Y ggtaacggtgtacactgtggaaaacattcatgtaccgtagactggggaacagctattggaaat
 G  N  G  V  H  C  G  K  H  S  C  T  V  D  W  G  T  A  I  G  N atcggaaataatgcagctgcaaactgggccacaggcggaaacgctggctggaataaataa
 I  G  N  N  A  A  A  N  W  A  T  G  G  N  A  G  W  N  K  *
```

EXPRESSION SYSTEM IN MICROORGANISM AND ITS USE FOR EXPRESSING HETEROLOGOUS AND HOMOLOGOUS PROTEINS

This application claims the benefit under 35 U.S.C. §371 of prior PCT International Application No. PCT/NO96/00266, which has an International filing date of Nov. 13, 1996, which designated the United States of America, the entire contents of which are hereby incorporated by references.

BACKGROUND OF THE INVENTION

The present invention relates to bacteriocins that are produced and secreted by various lactic acid bacteria. More specifically, it relates to the use of regulatory genetic elements (promoters) belonging to the genes that are involved in the production and secretion of bacteriocins. More specifically, it relates to the use of these genetic elements for the regulated expression of homologous or heterologous genes in lactic acid bacteria, in particular members of the genus Lactobacillus. Genes that have been manipulated in such a way as to put their expression under control of the invented genetic elements, as well as cells and vectors comprising such manipulated genes and a kit are also part of the present invention.

Cells produce proteins according to genetic information that is contained in the DNA. Many of these proteins catalyze chemical reactions in or outside the cells and are called enzymes. A piece of DNA that contains all the information for a protein is called a gene. A gene (DNA) is expressed as follows: first the process of transcription results in the formation of a so-called messenger RNA (mRNA); subsequently, in the process of translation, a protein (sometimes simply referred to as the gene-product) is synthesized, using the information contained in the mRNA.

To enable transcription, a gene is preceded by a promoter (=a piece of DNA preceding the gene that is not directly encoding the geneproduct but that is essential for initiation of transcritpion). In the process of transcription, the key enzyme involved in this process, RNA polymerase, associates with the promoter and, subsequently, a messenger RNA is synthesized. The extent to which a gene is expressed is often regulated at the transcriptional level; in other words, the level of transcription is regulated and this regulates the level at which the gene product is produced. Genes which are transcribed at a fixed (non-regulated) rate are said to be expressed constitutively. Regulation of transcription can be effectuated by regulating the association between the promoter and the RNA-polymerase. To achieve the latter a promoter element may contain stretches of DNA that 1) facilitate or impair association of RNA polymerase, or 2) permit the binding of additional factors (transcription factors) that enhance ('activator') or inhibit ('repressor') the binding of the RNA polymerase. In an alternative way of regulating gene transcription, the effectiveness of an associated RNA polymerase is regulated by binding of additional factors that, for example, prevent the associated RNA polymerase from actually starting the synthesis of an RNA molecule.

Bacteria can be made to produce certain proteins by introducing ('cloning') the corresponding gene in one or more copies. The gene may be maintained in the host organism either by using a plasmid, the vector, or by integrating it in the chromosome. To really obtain production of the desired geneproduct the cloned gene needs to be expressed. In most cases, this means that additional genetic engineering is necessary to put the cloned gene under the control of a specific promoter element that is recognized by the host organism. Such promoters may be regulable. These techniques of genetic manipulation can be used to establish two types of 'engineered' expression:

Homologous expression: an organism expresses a gene from the same species. The level of expression may for example be regulated by regulating the number of copies of the gene present per cell or by varying the promoter element by which the transcription of the gene is controlled.

Heterologous expression: as above, but now the gene that is expressed comes from a different species.

The establishment of the (regulable) expression of homologous or heterologous genes is an important part of genetic engineering in the biotechnological industry.

Temporal and quantitative regulation of gene expression is an important aspect of genetic engineering as employed in the biotechnological industry. Regulation can be an important problem, both in terms of timing of the expression and in terms of the quantity of expression. Really well regulable promoters applicable in industrially important microorganisms are therefore of major interest.

Lactic acid bacteria (LAB), such as members of the bacterial genera Lactococcus, Lactobacillus and Pediococcus are of major importance in fermentations conducted in the food and feed industry. Many LAB have the GRAS (Generally Regarded As Safe) status and they are consumed by humans regularity and in large amounts (for example in dairy products).

Many LAB produce bacteriocins, anti-microbial peptides that are harmless to humans (1,2). These peptides normally contain between 30 and 60 residues, they usually have a basic character, and, often, parts of their sequence show amphiphilicity when projected onto a helical wheel. Some bacteriocins undergo post-translational modification and are called lantibiotics. Bacteriocins are produced as precursor proteins with a leader peptide that is removed during export.

An expression system for Lactobacillus, Lactococcus and Bacillus is previously described in WO no. 94/00581 (VIAGEN OY). This expression system employs expression signals (promoters) linked to coat protein expression in Lactobacillus in combination with various secretion signals. This expression system does not employ regulable promoters. It provides some means for quantitative regulation of gene expression that are different from the means described in the present invention. It does not provide means for temporal regulation of gene expression. It is not based on promoters and regulatory mechanisms linked to bacteriocin production.

It is further published a paper by Djodevic, G. et al., "Cloning of promoter like sequences . . . *Lactobacillus paracasei* subsp. . . . ", Can. J. Microbiol. (1994), 40 (12), 1043–50. This publication relates to gene expression in Lactobacillus but does not describe or suggest means to regulate gene expression temporarily, as is done in the present invention. Furthermore, this publication concerns normal, non-regulable promoters that give raise to constitutive, non-regulable expression in Lactobacillus.

It is further published a paper by Tizacheck, P. S., Vogel, R. F. and Hammes, W. P., "Cloning and sequencing of SAKP encoding sakacin-P, the bacteriocin produced by *Lactobacillus sake* LTH673", Microbiology-UK (1994) V140, FEB (FEB), 361–67, and there is an entry in the EMBL/GenBank/DDBJ database (accession number Z48542)(SEQ ID NOS: 13–19) by Huehne, K., Holck, A., Axelsson L. and Kroeckel, L. (1995). These two publications describe the nucleotide sequences of pieces of DNA from, respectively, *Lactobacillus sake* LTH673, and *Lactobacillus sake* Lb674, that are, within the experimental error, identical and that encode genes involved in the production of bacteriocin, called sakacin P. These nucleotide sequences do also contain the promoter sequences depicted in FIG. 4 (the upper four sequences). However, these publications do only describe sequences; they do not describe: 1) the regulatory mechanism for gene expression that is part of the present invention, 2) the promoter elements involved in this regulatory mechanism that are part of the present invention, 3) the expression-inducing peptides that are part of the present invention, 4) possible applications of the regulatory mechanisms referred to in points 1–3. In other words these publications do not relate to the regulation of gene expression in Lactobacillus by use of specific regulable promoters, nor do they describe such promoters. In other words: knowing the sequences of genes involved in the production of bacteriocins, including the sequences upstream of those genes (that contain promoter elements) is in itself not enough to recognize (1) the regulatory mechanism involved in the regulation of the expression of genes involved in bacteriocin production, (2) the regulable promoter elements involved, or (3) the biotechnological potential of this regulatory mechanism.

In N. Balaban and R. P. Novick (Proc. NAtl. Acad. Sci. USA, 92; 1919–1623 (1995)) it is suggested that the production of exproteins in *Staphylococus aureus*, which is known to be controlled by a global regulatory system, agr, depends on autoinduction by a proteinaceous factor produced and secreted by the bacteria. The proteinaceous factor that was only suggested in above publication. The *S. aureus* system differs essentially from the system described in the present invention in that (1) the regulatory mechanisms in *S. aureus* are more complex, for example because they involve a modified peptide and regulatory RNA molecule,
(2) in contrast to LAB, *S. aureus* is a pathogenic bacterium,
(3) the production and secretion of the inducer peptide in *S. aureus* occurs by a different mechanism (involving gene-products that do not occur in the systems described in the patent) than the production and secretion of the inducer peptide in LAB, and
(4) application of the *S. aureus* system in LAB is not feasible, because of complications resulting from what is described under the previous three points.

In CA, 121(1) 4725e it is described regulation of nisin biosynthesis in *Lactococcus lactis*, wherein genes nisK and nisR encode two proteins that compose a classical two-component signal transduction system. In the nisin system, the bacteriocin itself (nisin) is the inducing substance, making this system essentially different from the present invention. Furthermore, nisin is a modified peptide that can not easily be obtained by peptide sysnthesis such as the inducer peptides described in the present invention. Natural production of nisin depends on mechanisms for modification and secretion that are different or absent in the systems described in the patent application. The nisin system is based on promoter elements different from the Lactobacillus system of the present invention.

These objects are obtained by the present invention characterized by the enclosed claims.

BRIEF DESCRIPTION OF THE INVENTION

The present invention relates to a gene expression system, which comprises genes, promoter sequences and peptides involved in the production of bacteriocins except nisin in lactic acid bacteria. In other aspects of the invention the expression system contains at least one specific regulated promoter, genes involved in transducing signals that induce gene expression, a peptide being that signal, and, possibly, genes involved in producing, processing, and secreting this inducing peptide.

The invention relates furthermore to a recombinant vector comprising any possible combination of certain genes and certain promoter elements a host cell which is transformed with the recombinant vector and is selected from the group consisting of members of the genera Lactobacillus, Lactococcus, Pediococcus, a purified peptide that can induce gene expression and that may be expressed by the host cells, and to purified protein which is produced by the host cells.

The invention relates also to the use of the gene expression system in any of the above host cells, use of the host cells in fermentations and use of the host cell to produce a desired protein.

Still another aspect of the invention is a kit for using the expression system in lactid acid bacteria, which consists of:

1) One or more recombinant vectors each containing a promotor element identical or similar to one of the elements depicted in FIG. 4, directly followed by a multiple cloning site; these vectors may also contain one or more genes selected from the group K, R, IF, T, A (FIG. 1) or functional analogues of these genes,
2) Lactic acid bacteria that can function as host strain for these recombinant vectors, and that, depending on the recombinant vector used, may contain one or more genes selected from the group K, R, IF, T, A (FIG. 1) (or functional analogues of these genes) integrated in the chromosome,
3) A peptide that is capable of inducing the expression of genes under control of promoter elements similar or identical to the promoter elements depicted in FIG. 4 and that needs a two component system similar or identical to that encoded by genes K and R (FIG. 1) to exert its inducing action.

BRIEF DESCRIPTION OF THE DRAWINGS

In the following the invention will be disclosed in more detail in which the figures exhibit:

FIG. 1. Genetic organization of the genes involved in sakacin P production by *Lactobacillus sake* strain LTH673 (this bacterial strain is described in references 7 and 8). The open arrows indicated genes that are named by a letter below the arrow. The P's above the open arrows indicate promoter elements (FIG. 4). The thin closed arrows indicate transcripts that can be detected by Northern blotting in induced LTH673 cells. See text for details. Sequence length is indicated by the lower line that represents 10000 bases.

FIG. 2. Nucleotide (SEQ ID NO:2) sequence of the IF gene (see FIG. 1) and sequence of the encoded peptide (SEQ ID NO:3). This gene encodes the inducing peptide. The two glycine residues that are characteristic for the so-called 'double glycine type' leader peptide that is cleaved off during secretion are printed in bold. The first amino acid residue of the secreted 19-residue peptide is underlined.

FIG. 3. Nucleotide sequence (SEQ ID NO:4) of the P gene (see FIG. 1) and sequence of the encoded peptide (SEQ ID NO:5). This gene encodes sakacin P. The two glycine residues that are characteristic for the so-called 'double glycine type' leader peptide that is cleaved off during secretion are printed in bold. The first amino acid residue of the secreted sakacin P is underlined.

FIG. 4. Regulable promoter element. The following promoter elements are shown: IF: in front of gene IF (SEQ ID NO:6) (FIG. 1); sakP (SEQ ID NO:7): in front of gene P (FIG. 1); transport (SEQ ID NO:8); in front of gene T (FIG. 1); BacX (SEQ ID NO:9): in front of an other regulated gene from *Lactobacillus sake* LTH673 (not discussed in this invention); plnA: in front of genes involved in bacteriocin production in *Lactobacillus plantarum* C11; (9, 12) AgrB (SEQ ID NO:11), hld (SEQ ID NO:12): in front of genes from *Staphylococcus aureus*, whose expression is regulated in a growth-phase dependent way. Characteristics of the promoter elements (conserved sequences/repeats, characteristic spacing between conserved elements) are indicated. The t and a dominated region marked by −10 is the so-called TATA box normally found at approximately 10 bases in front of the transcriptional starting point. The N indicates the transcription starting point, as determined by primer extension analysis. N is the first nucleotide of the transcripts indicated in FIG. 1.

DETAILED DESCRIPTION OF THE INVENTION

Figure 4:
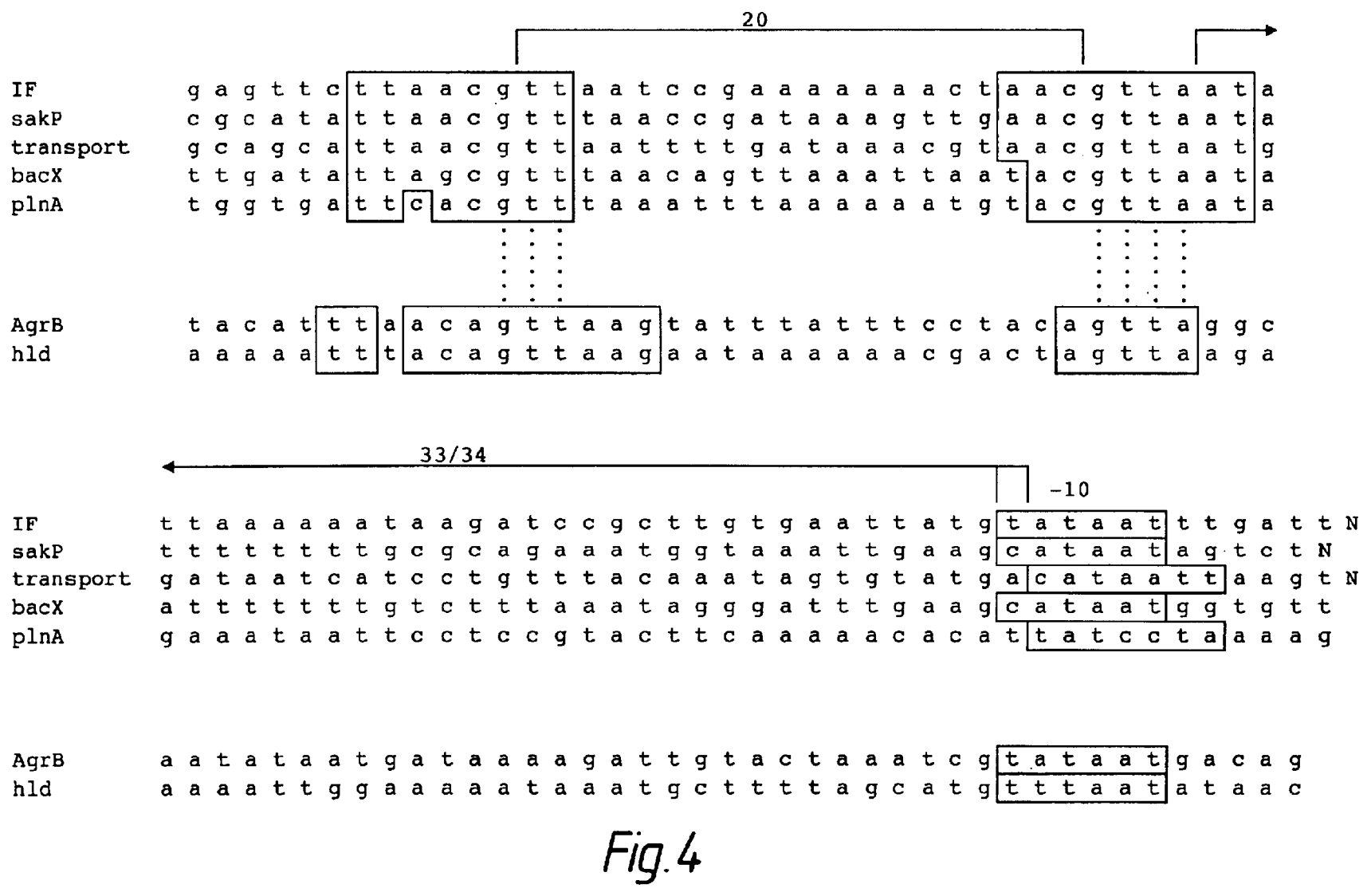
Figure 5:
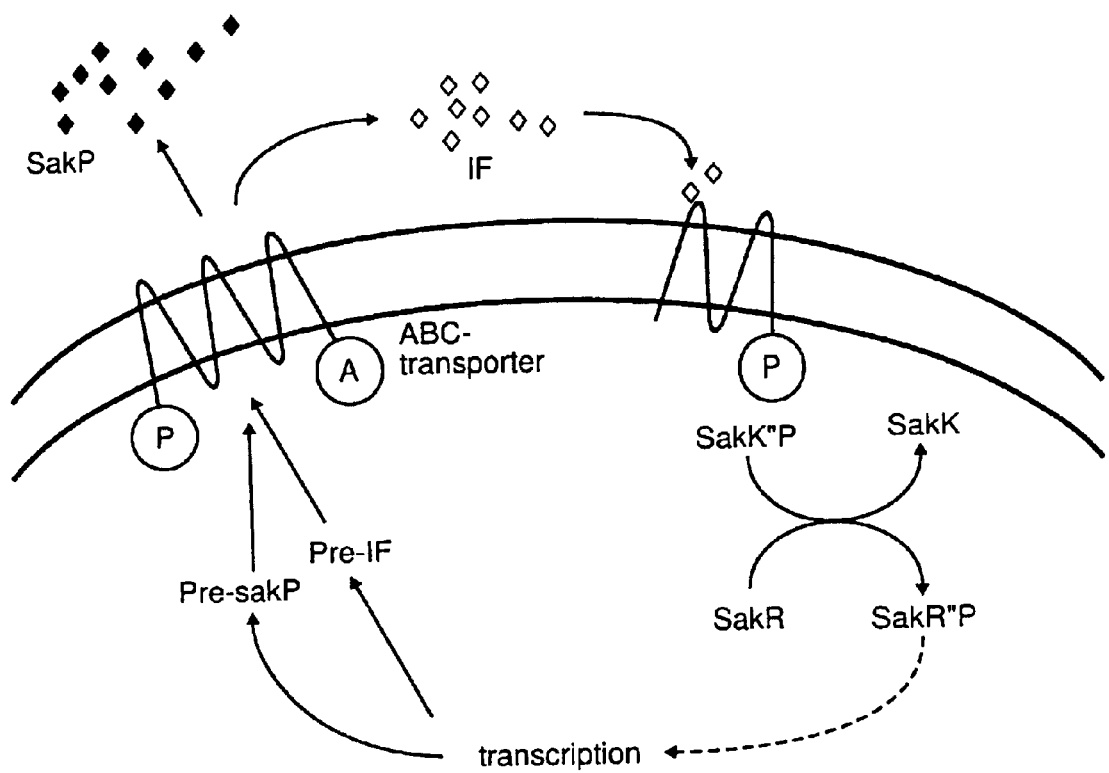
FIG. 5. Simplified, partly hypothetical model for the regulatory mechanism involved in sakacin P production in *Lactobacillus sake* LTH673. Codes: SakP: secreted sakacin P, processed product of gene P (FIG. 1); Pre-sakP: primary (non-processed) product of gene P; IF: secreted inducing peptide, processed product of gene IF (FIG. 1); Pre-IF: primary (non-processed) product of gene IF; ABC-transporter: product of gene T (FIG. 1); SakK-P and SakK: product of gene K (FIG. 1; histidine kinase) in an activated (phosphorylated) and inactivated form, respectively; SakR-P and SakR: product of gene R (FIG. 1; response regulator) in an activated (phosphorylated) and inactivated form, respectively.

The present invention concerns the discovery of a new regulatory mechanism for gene expression in LAB (depicted in simplified form in FIG. 5) that includes previously unrecognized, strongly regulable promoter elements (FIG. 4). The essential finding is that the expression of genes under the control of the promoter element depicted in FIG. 4 is dependent on the expression of the IF-K-R gene cluster (FIG. 1) or an analogue thereof, for example from other bacteriocin producing strains (for example the plnABCD gene cluster present in *Lactobacillus plantarum* C11; ref. 12). The expression of the IF-K-R gene cluster is autoinduced by the secreted peptide encoded by IF. Thus, the expression of a gene under control of the promoter element depicted in FIG. 4 in cells that contain the appropriate K and R gene can be induced at will by adding the cognate, chemically synthesized (harmless) inducing peptide, for example, in the case of the IF-K-R set found in *Lactobacillus sake* LTH673 (FIG. 1), the 19-residue peptide (residues 19 through 37 of SEQ ID NO:3) depicted in FIG. 2. The bacterial strain *Lactobacillus sake* LTH673 is described in detail in references 7 and 8 and will hereafter now and then be referred to as LTH673.

The second essential element of the present invention is a long range of applications that is conceivable on the basis of the newly discovered regulatory mechanism and promoter elements. This is illustrated by the following example: One could construct a plasmid that contains 1) the LTH673 K and R genes under control of a constitutive promoter, plus 2) a cloned gene encoding a desired enzymatic property under control of the promoter element depicted in FIG. 4. One could then use transformation to introduce this plasmid in a Lactobacillus (or other LAB) strain in which genes under control of the promoter element depicted in FIG. 4 are normally switched off. The enzymatic activity encoded by the cloned gene can now be switched on at will, by adding the 19-residue inducing peptide depicted in FIG. 2. Quantities of inducing peptide needed are low and the costs of using this chemically synthesized compound are therefore low.

Many variations in this example are conceivable. They concern for example 1) the promoter used to express K and R, 2) the exact promoter used to express the desired enzymatic activity (there are small differences between the promoter elements depicted in FIG. 4), 3) the number of genes involved in the genetic constructions (instead of K and R, one could also use IF, K, and R in a LAB strain that has the ability to cleave of the IF leader peptide; this would give a more autoinducible character to the engineered system) and 4) the genetic methods used (genes can be maintained in the host cells by using plasmid vectors and/or by integrating them into the chromosome). The use of chromosomal integration to establish the regulated expression of a desired enzymatic property in LAB would result in highly stable, fully food grade genetically manipulated bacterial strains.

The present inventors have discovered the following:

1. The genetic information that is necessary for the production of bacteriocin (called sakacin P) by *Lactobacillus sake* strain LTH673 (7, 8) (hereafter called 'LTH673') contains at least the genes depicted in FIG. 1. Other workers have shown that the genes depicted in FIG. 1 are all the genes that are needed for sakacin P production and that every individual gene depicted in FIG. 1 is essential for sakacin P production.

2. The genes that are necessary for bacteriocin production are:

IF: encoding a 37-residue peptide of which the first 18 residues form a typical so-called 'double-glycine type' leader peptide directing secretion and processing. This suggests that expression of this gene could result in the secretion of a 19-residue peptide (residues 19 through 37 of SEQ ID NO:3) (FIG. 2).

K: encoding a protein that resembles a so-called histidine kinase, known to be involved in cellular responses to environmental signals (4, 5, 6).

R: encoding a so-called response regulator, often found together with a histidine kinase and known to mediate cellular response by stimulating or repressing transcription starts at specific (regulated) promoters (4, 5, 6).

P: The structural gene for sakacin P. The N-terminal part of the peptide encoded by this gene is a typical 'double glycine type' leader peptide that directs secretion and processing of sakacin P (FIG. 3).

I: Gene encoding an immunity protein which prevents the LTH673 cells to be killed by the bacteriocin (sakacin P) that they produce.

T,A: Encode two proteins known to be involved in the secretion and processing (=cleaving off the leader peptide) of sakacin P and the 19-residue peptide (the latter is an assumption based on the fact that the bacteriocin and the 19-residue peptide are preceeded by functionally identical leader peptides). The protein encoded by T is known to catalyze the cleaving off of the leader peptide during the process of secretion (3, 10, 13, 14).

3. The supernatant of bacteriocin producing LTH673 cultures not only contains sakacin P, but also a peptide identical to the 19-residue peptide depicted in FIG. 2.

Both sakacin P and this peptide can be purified from such a supernatant.

4. Upon strong dilution LTH673 cells lost their ability to produce bacteriocin, despite the fact that the dilution does not affect the genetic contents of the cells. Concomitantly, the cells stopped producing the 19-residue peptide and they lost their immunity towards sakacin P. The production of bacteriocin and the 19-residue peptide, as well as immunity towards sakacin P could be restored by adding the 19-residue peptide depicted in FIG. 2 (either purified peptide or peptide obtained by chemical synthesis). This indicates that the 19-residue peptide induces transcription of the genes involved in bacteriocin production.

5. In bacteriocin deficient cultures of LTH673, transcription of the genes depicted in FIG. 1 could not be detected (by Northern blotting). Upon adding the 19-residue peptide to such cultures (purified or synthetic) several transcripts could be detected, as indicated in FIG. 1.

6. Observations essentially similar to the ones described under points 1–5 have been made in relation to bacteriocin production by *Lactobacillus plantarum* C11, (9). The genetic organization and the regulatory events described under points 1–5 are likely to occur in many bacteriocin producing lactobacilli and, possibly, LAB in general.

7. The transcription events that are initiated by the 19-residue peptide in LTH673 all start at promoters (indicated by P in FIG. 1) that bear only moderate resemblance to normal, non-regulated promoters found in LAB. The promoter regions do however contain conserved stretches of sequence that by their general character (i.e. direct repeats are present; see FIG. 4) indicate a regulatory function. The promoter regions are depicted in FIG. 4. The conserved promoter regions depicted in FIG. 4 and/or their regulatory function have not been recognized as such previously.

8. The identification of these regulatory promoter elements subsequently permitted (by sequence comparison) the detection of similar elements in front of regulated genes involved in bacteriocin production by *Lactobacillus plantarum* C11, (9, 12) and in front of genes from *Staphylococcus aureus* (11), the expression of which is known to be temporally regulated (FIG. 4). Genetic analysis of the genes involved in bacteriocin production in *Lactobacillus plantarum* C11 has shown that this bacterium produces a peptide that is functionally similar to the 19-residue peptide depicted in FIG. 2.

9. The effect of the 19-residue peptide on gene expression must be mediated by the so-called two-component regulatory system (4, 5, 6) encoded by the K and R genes depicted in FIG. 1. Based on generally accepted ideas concerning the function of two-component regulatory systems (4, 5, 6), the mechanism of induction would be the following (FIG. 5): The product of gene K 'senses' the 19-residue peptide, which results in the activation of the product of R. The product of R acts on the promoter elements depicted in FIG. 4 either directly, as an activator, or indirectly, by binding to a repressor that untill the moment of induction prevents transcription. It should be noted that the conclusion that the gene products of IF, K, and R (FIG. 1) are enough to induce transcription of a gene that is preceded by the promoter element depicted in FIG. 4 is under investigation. It is therefore possible that the product of a hitherto unknown gene is also required. In the description of this invention a reference to the group IF, K and R should therefore be interpreted as a reference to IF, K, R and such a possible extra gene if it would appear to exist.

10. These discoveries indicate that under natural conditions (that differ largely from laboratory and industrial fermentation conditions) the regulatory mechanism identified here serves to give the bacterium a selective advantage. Bacteriocins inhibit the growth of bacterial species closely related to the producing organism and thus provide this organism with a selective advantage over its natural competitors. The sensing of its own growth, which is likely to be comparable to that of competing species in the same medium, would enable the producing organism to switch-on the production of anti-microbial activity at higher cell densities, when the competition for nutrients becomes more severe. Such quorum sensing could be based on a slow accumulation of the inducing peptide (the product of the IF gene in FIG. 1) in the early stages of growth as a result of low constitutive production. At a certain point the accumulated peptide then triggers an autoinduction pathway resulting in increased expression of genes encoding the inducing peptide itself (IF, FIG. 1), the bacteriocin and corresponding immunity protein (P, I), the processing and transport machinery for both the bacteriocin and the inducing peptide (T, A) (3, 10, 13, 14), and the two-component system that transduces the induction signal (K, R) (4, 5, 6) (FIG. 5).

The present invention has several areas of application.

With the current state of technology it is very difficult to establish gene expression in LAB in a way that permits detailed temporal and/or quantitative regulation of expression. The present invention can be used generally for the temporal and, possibly, quantitative regulation of gene expression in Lactobacillus and, possibly, other LAB. The invention thus can be applied in all kinds of industrial processes and types of scientific research. Below a few obvious (A) and a few more far-fetched (B) examples of applications are given:

A. A gene encoding an important enzymatic activity can be put under the control of the regulable promoter element and introduced in a LAB strain that is used in an industrial fermentation. The enzymatic activity in the fermentation can then be temporally regulated since this activity will only become available after the fermentation operator induces gene expression by adding the inducing peptide. Manipulation of the fermentation temperature and/or the inducing peptide dose may in addition permit accurate regulation of the amount of enzymatic activity that is produced. Further research may also result in ways to switch off gene expression at desired time-points, for example by changing the temperature at which the fermentation is conducted. Interesting enzymatic activities are for example:

Proteolytic activity; for example for the regulation of production speed and taste in the production of yoghurt and cheese.

Carbohydrolytic activity; for the regulation of product sweetness.

Autolytic activity; autolysis causes cell death, meaning that autolysis genes placed under control of the regulated promoter permits the fermentation operator to induce cell death (and thus inhibit growth of particular types of bacteria in the fermentation) at desired time-points.

Interesting non-enzymatic traits that could be regulated are for example:

The production of vitamins; thus, the nutritional content of the fermentation medium can be manipulated.

The production of bacteriocins; this would enable to induce growth inhibition of certain strains in the fermentation at specific time-points.

B. Many LAB, including Lactobacillus colonize the human intestine and they are a natural part of our intestinal flora. Relationships between health and the LAB content of intestinal flora are studied intensively. Because of their capacity to colonize the intestine LAB have potential as drug-delivery-system and as vaccines (=LAB expressing an antigen on its surface). The regulatory mechanism decribed in the present invention is a cell-density sensing system and it could thus be used to make the expression of a certain gene dependent on a certain degree of colonization (cell density). For the application of LAB in humans it is very important to know details about their survival in and colonization of the human gastro-intestinal tract. In The Netherlands an artificial human gastro-intestinal tract (made of glass) has been built to investigate the survival and colonization of LAB in the human body. LAB concentrations in the gastro-intestinal tract are determined by (laborious) plating of samples obtained after opening the artificial tract. For these kind of studies it would be possible to couple the regulated promoter invented here to a gene encoding proteins that can emit light by fluorescence. In principle, this could permit the registration of the colonization and survival rate of LAB by simply looking at the artificial gastro-intestinal tract and by measuring light emission.

EXAMPLES

The examples below are for illustrative purposes only and are not deemed to limit the scope of the invention.

Example 1

Detection of a Regulatory Mechanism for Bacteriocin Production in *Laciobacillus sake* LTH673

We possessed a so called 'glycerol-stock' (kept at −80° C.) of a bacterial strain called *Lactobacillus sake* LTH673 (refs. 7,8) that was originally isolated as a bacteriocin producer. This bacteriocin was later shown to be sakacin P (ref. 8). Bacterial cultures obtained by inoculating MRS medium (Difco Laboratories, Detroit, Mich., USA; or Oxoid ltd. Basingstoke, Hampshire, England) with material from this glycerol-stock produced sakacin P (Bac$^+$ phenotype) and, accordingly, were immune to purified sakacin P.

The Bac$^+$ phenotype of cells in this bacterial culture was lost upon diluting a Bac$^+$ LTH673 culture more than ~2000-fold in fresh MRS-medium. Likewise, colonies obtained upon plating cells from a Bac$^+$ LTH673 culture had a Bac$^-$ phenotype. Loss of the Bac$^+$ phenotype upon dilution or plating could be prevented by adding supernatant of an overnight Bac$^+$ LTH673 culture at an end concentration of minimally 0.05% (v/v). Furthermore, such a supernatant could induce bacteriocin production in Bac$^-$ cultures obtained after inoculating fresh medium with a Bac$^-$ colony. Colonies obtained after plating cells from a Bac$^-$ culture in the presence of supernatant from a Bac$^+$ culture all were Bac$^+$. These observations suggest that the medium of a Bac$^+$ LTH673 culture contains a component that is indispensable for maintaining and inducing bacteriocin production. The inducing component was lost after treatment of culture medium with proteinase K, but not after boiling for 10 minutes, indicating that it could be a peptide.

As indicated above Bac$^-$ colonies of *Lactobacillus sake* LTH673 were obtained after plating cells from a Bac$^+$ culture. Cultures obtained after inoculating MRS medium with such a Bac$^-$ colony had a Bac$^-$ phenotype and they kept this phenotype during many generations. Glycerol stocks of such Bac$^-$ cultures were made and fresh cultures obtained after inoculating MRS medium with an inoculum from such a glycerol stock again were Bac$^-$. In all cases tested, the only way to restore bacteriocin production was to add supernatant of a Bac$^+$ culture that thus, apparently, contains an inducing substance.

*Lb. sake* LTH673 (Bac$^+$) is immune to purified sakacin P and to several related purified bacteriocins. Immunity is caused by a specific protein that is produced concomitantly with the bacteriocin. Accordingly, we observed that the loss and induction of the Bac$^+$ phenotype was invariably accompanied by, respectively, the loss and induction of immunity to sakacin P. Another trait invariably linked to changes in the Bac phenotype was the inducing capacity itself: this capacity was only present in supernatants of Bac$^+$ cultures but not in the supernatants of Bac$^-$ cultures.

Thus, the culture supernatant of Bac$^+$ cultures of *Lactobacillus sake* LTH673 contains an inducing factor that is indispensible for sakacin P production. This factor induces its own production concomitantly with sakacin P production and immunity to sakacin P.

Example 2

Purification and Characterization of a Pepide Inducing Bacteriocin Production in *Lactobacillus sake* LTH673

One liter of MRS-broth was inoculated with 10 ml of a bacteriocin-producing overnight culture of *Lb. sake* LTH673 and incubated at 30° C. for eight hours. The supernatant was collected by centrifugation (30 minutes, 12000 g) and proteinaceous material was precipitated with ammonium sulfate (50% saturation). The precipitate was collected by centrifugation (30 minutes, 12000 g), dissolved in 200 ml buffer A (10 mM sodium phosphate, pH 5.5), and applied to a 10 ml column of S-Sepharose Fast Flow (Pharmacia-LKB, Uppsala, Sweden) equilibrated with buffer A. The column was washed with 200 ml buffer A after which material bound to the column was eluted by applying 50 ml of buffer A containing 1 M NaCl. The eluate (50 ml) was supplemented with 5 g ammonium sulfate and applied to a 10 ml Octyl-Sepharose (Pharmacia-LKB) column equilibrated in buffer A containing 10% (w/v) ammonium sulfate. The inducing factor was eluted in a broad peak by applying a linear gradient from 100% starting buffer, to 100% water. Fractions containing the highest IF concentrations were diluted two-fold with a 0.1% (v/v) TFA solution and applied to a $\mu C_2/C_{18}$ reverse-phase column (SC 2.1/10) equilibrated in 0.1% (v/v) TFA and inserted in a Smart System (Pharmacia-LKB). The peptide was eluted with a linear gradient ranging to 50% (v/v) 2-propanol, 0.1% (v/v) TFA. All steps were performed at room temperature.

The amino acid sequence of the purified material was determined using a model 477A sequencer (Applied Biosystems, Foster City, USA) and found to be: Met-Ala-Gly-Asn-Ser-Ser-Asn-Phe-Ile-His-Lys-Ile-Lys-Gln-Ile-Phe-Thr-His-Arg (19 residues, residues 19–37 of SEQ. ID. NO:

3) with a calculated molecular weight of 2229.6. This amino acid sequence corresponds with the amino acid sequence encoded by part the DNA sequence that was determined for DNA from *Lactobacillus sake* LTH673 (FIG. 2).

Mass spectrometry was performed using a PE Sciex API 1 electrospray mass spectrometer. Mass spectrometry indicated a molecular weight of 2244.8+/−0.6, which is in good agreement with the calculated molecular weight, assuming that the N-terminal methionine residue is oxidized.

Addition of the purified peptide to *Lactobacillus sake* LTH673 cells that did not produce bacteriocin, nor the inducing peptide, nor were immune to sakacin P resulted in the induction of
1) sakacin P production,
2) production of the inducing peptide itself, and
3) induction of immunity to sakacin P.

Thus, the inducing factor detected in culture supernatants of Bac+ cultures of *Lactobacillus sake* LTH673 (example 1) and the purified 19-residue peptide must be one and the same.

Thus, the expression of several genes involved in bacteriocin production and immunity was switched on by adding the purified inducing peptide to Bac− cultures of *Lactobacillus sake* LTH673.

It will be understood by those with skill in the art that the expression of other genes that are
1) placed under control of the same regulated promoter elements as the genes involved in bacteriocin production, and
2) introduced in non-bacteriocin producing *Lactobacillus sake* LTH673 cells can also be induced by adding the purified inducing peptide.

Example 3

Regulation of Bacteriocin Production in *Lactobacillus plantarum* C11

Experiments similar to the ones described in examples 1 and 2 were conducted with the bacteriocin producing strain *Lactobacillus plantarum* C11. These experiments yielded results that were essentially similar to the results described in examples 1 and 2. The sequence of the amphiphilic inducing peptide for the *Lactobacillus plantarum* C11 regulatory system is: Lys-Ser-Ser-Ala-Tyr-Ser-Leu-Gln-Met-Gly-Ala-Thr-Ala-Ile-Lys-Gln-Val-Lys-Lys-Leu-Phe-Lys-Lys-Trp-Gly-Trp (26 residues) (SEQ. ID. NO: 1).

It will be understood by those with skill in the art that the expression of other genes that are
1) placed under control of the same regulated promoter elements as the genes involved in bacteriocin production, and
2) introduced in non-bacteriocin producing *Lactobacillus plantarum* C11 cells can also be induced by adding this 26 residue inducing peptide.

Example 4

Analysis of the Genes and Promoters Involved in the Production of Sakacin P by *Lactobacillus sake* LTH673 and Analysis of the Transcription of those Genes as Initiated by those Promoters The genetic information that is necessary for the production of bacteriocin (called sakacin P) by *Lactobacillus sake* strain LTH673 (hereafter called 'LTH673') contains at least the genes depicted in FIG. 1. Other workers have shown that the genes depicted in FIG. 1 are all the genes that are needed for sakacin P production and immunity, and that every individual gene depicted in FIG. 1 is essential for sakacin P production and immunity.

The genes that are necessary for bacteriocin production are:
IF: encoding a 37-residue peptide of which the first 18 residues form a typical so-called 'double-glycine type' leader peptide (ref. 3) directing secretion and processing. This suggests that expression of this gene could result in the secretion of a 19-residue (residues 19 through 37 of SEQ ID NO:3) peptide identical to the peptide described in example 2 (FIG. 2).
K: encoding a protein that resembles a so-called histidine kinase, known to be involved in cellular responses to environmental signals (refs. 4,5,6).
R: encoding a so-called response regulator, often found together with a histidine kinase and known to mediate cellular response by stimulating or repressing transcription starts at specific (regulated) promoters (refs. 4,5,6).
P: The structural gene for sakacin P. The N-terminal part of the peptide encoded by this gene is a typical 'double glycine type' leader peptide (ref. 3) that directs secretion and processing of sakacin P (FIG. 3).
I: Gene encoding an immunity protein which prevents the LTH673 cells from being killed by the bacteriocin (sakacin P) that they produce.
T,A: Encode two proteins known to be involved in the secretion and processing (=cleave off the leader peptide) of sakacin P and the 19-residue peptide (the latter is an assumption based on the fact that the bacteriocin and the 19-residue peptide are preceeded by functionally identical leader peptides. The protein encoded by T is known to catalyze the processing of the leader peptide during the process of secretion (refs. 3,10,13,14).

In cultures of *Lactobacillus sake* LTH673 with the Bac− phenotype, transcription of the genes depicted in FIG. 1 could not be detected at any stage during growth (by Northern blotting). After adding the 19-residue peptide described in example 2 to such cultures (purified or synthetic) several transcripts could be detected within 30 minutes (by Northern blotting), as indicated in FIG. 1.

Using so-called primer extension analyses, the start-point of transcription was determined for the transcripts indicated in FIG. 1. These start points are indicated in FIG. 4. The start-points are by definition preceded by the promoter region.

The promoter regions in front of the transcription start points (indicated by 'P' in FIG. 1; shown in detail in FIG. 4) bear only moderate resemblance to normal, non-regulated promoters found in LAB. Such normal promoters contain so-called −35 and −10 regions that are recognizable since they are similar in most promoters. The promoter regions depicted in FIG. 4 do contain a normal −10 region, but they do not have an easy recognizable −35 region. The promoter regions do however contain conserved stretches of sequence, with conserved spacing between these stretches, that seem to be an essential element of their regulable character, since:
1) they are conserved in all three sakacin P related promoter elements, and
2) their general character indicates a possible regulatory function The recognition of the regulatory promoter elements in the sakacin P related genes subsequently permitted (by sequence comparison) the detection of similar elements in front of regulated genes involved in bacteriocin production by *Lactobacillus plantarum* C11 and in front of genes from *Staphylococcus aureus*, the expression of which is known to be temporally regulated (FIG. 4).

The conserver promoter regions depicted in FIG. 4 and/or their regulatory function have not been recognized as such previously.

It should be noted that the identification of the common characteristics in regulable promoter elements that are indicated in FIG. 4 could only occur after I) identification of the regulatory mechanism illustrated by examples 1, 2 and 3, II) analysis of transcripts in Bac⁻ and Bac⁺ *Lactobacillus sake* LTH673 cells by Northern blotting, and comparison of the results obtained for Bac⁻ and Bac⁺ cells.

III) determination of transcription initiation points by primer extension analysis, in Bac⁻ and Bac⁺ *Lactobacillus sake* LTH673 cells, and comparison of the results obtained for Bac⁻ and Bac⁺ cells, and IV) analysis of the gene cluster depicted in FIG. 1, with the knowledge gained from the three discoveries (I, II, and III) mentioned directly above at hand.

It will be understood by those with skill in the art that the expression of other genes that are 1) preceded by promoter elements similar to the ones depicted in FIG. 4, and
2) introduced in non-bacteriocin producing *Lactobacillus sake* LTH673 cells can be induced by adding the 19-residue inducing peptide (residues 19 through 37 of SEQ ID NO:3) described in example 2.

Example 5

Synthesis of a Peptide Inducing Bacteriocin Production in *Lactobacillus sake* LTH673

A 19-residue peptide with the sequence and calculated molecular weight described in example 2 was synthesized. Its molecular weight was determined to be 2229.5 by mass spectrometry, which is, within experimental error, in accordance with the calculated molecular weight. This peptide had the same inducing effects as 1) culture supernatants of Bac⁺ cultures of *Lactobacillus sake* LTH673, and 2) the purified peptide described in example 2, in *Lactobacillus sake* LTH673.

Thus, this synthetic peptide can be used to induce and/or maintain the expression of genes involved in the production of sakacin P by *Lactobacillus sake* LTH673.

It will be understood by those with skill in the art that the expression of other genes that are 1) preceded by promoter elements similar to the ones depicted in FIG. 4, and
2) introduced in non-bacteriocin producing *Lactobacillus sake* LTH673 cells can be induced by adding this synthetic 19-residue inducing peptide.

Example 6

Analysis of the Genes and Promoters Involved in the Production of Bacteriocins by *Lactobacillus plantarum* C11 and Analysis of the Transcription of those Genes Observations essentially similar to the ones described by examples 1,2, and 4 have been made in relation to bacteriocin production by *Lactobacillus plantarum* C11. This strain produces a large number of bacteriocins, corresponding immunity proteins, and the 26-residue inducing peptide described in example 3. The corresponding genes have been cloned and sequenced. These genes are not expressed in Bac⁻ cultures of *Lactobacillus plantarum* C11; however gene expression can be induced by adding the 26-residue inducing peptide described in example 3. Promoter elements in front of the transcription start-points resemble those found in front of the genes involved in sakacin P production, as indicated in FIG. 4.

It will be understood by those with skill in the art that the expression of other genes that are 1) preceded by promoter elements similar to the ones depicted in FIG. 4, and
2) introduced in non-bacteriocin producing *Lactobacillus plantarum* C11 cells can be induced by adding the 26-residue inducing peptide described in example 3.

The genetic organization and the regulatory events described by examples 1,2,4, and 6 are likely to occur in many bacteriocin producing lactobacilli and, possibly, LAB in general. It will be understood by those with skill in the art that the regulatory processes described in the present invention and the possible applications thereof may be accomplished by any set of genes and inducing peptides from LAB that have functions that are analogous to the functions of the genes described in examples 4 and 6, and the peptides described in examples 2 and 3.

Peptides analogous to the peptides described in examples 2 and 3 are: peptides from LAB that 1) are secreted via a typical so-called 'double glycine type' leader peptide,
2) are encoded by a gene that is co-transcribed with genes encoding parts of a so-called two-component regulatory system and/or with genes involved in bacteriocin production, and
3) can induce gene expression under certain conditions.

Example 7

Synthesis of Peptides Inducing Bacteriocin Production in *Lactobacillus plantarum* C11

A 26-residue peptide (SEQ ID NO:1) with the sequence given in example 3 was synthesized. This peptide had the same inducing effects as 1) culture supernatants of Bac⁺ cultures of *Lactobacillus plantarum* C11, and 2) the purified peptide described in example 3, in *Lactobacillus plantarum* C11.

Thus, this synthetic peptide can be used to induce and/or maintain the expression of genes involved in the production of bacteriocins by *Lactobacillus plantarum* C11.

It was shown that shorter variants (truncation of three or four amino acids at the N-terminus) of this peptide also can induce bacteriocin production in *Lactobacillus plantarum* C11.

It will be understood by those with skill in the art that the expression of other genes that are 1) preceded by promoter elements similar to the ones depicted in FIG. 4, and
2) introduced in non-bacteriocin producing *Lactobacillus plantarum* C11 cells can be induced by adding this synthetic 26-residue inducing peptide (or somewhat shortened variants thereof).

Example 8

Most Likely Mechanism for the Regulation of Bacteriocin Production in *Lactobacillus sake* LTH673, *Lactobacillus plantarum* C11, and, Possibly, Other LAB, as Derived from the Results Described in Examples 1–7, and the Consequences of this Mechanism for its Application The effect of the 19-residue peptide (residues 19 through 37 of SEQ ID NO:3) on gene expression in *Lactobacillus* sake LTH673 must be mediated by the so-called two-component regulatory system (refs. 4,5,6) encoded by the K and R genes depicted in FIG. 1. Based on generally accepted ideas concerning the function of two-component regulatory systems (refs. 4,5,6), the mechanism of induction would be the following (FIG. 5): The product og gene K 'senses' the 19-residue peptide, which results in the activation of the product of R. The product of R acts on the promoter elements depicted in FIG. 4 either direct, as an activator, or indirect, by binding to a repressor that untill the moment of induction prevents transcription.

These discoveries indicate that under natural conditions (that differ largely from laboratory and industrial fermentation conditions) the regulatory mechanism identified here may serve to give the bacterium a selective advantage. Bacteriocins inhibit the growth of bacterial species closely related to the producing organism and thus provide this organism with a selective advantage over its natural competitors. The sensing of its own growth, which is likely to be comparable to that of competing species in the same medium, would enable the producing organism to switch-on the production of anti-microbial activity at higher cell densities, when the competition for nutrients becomes more severe. Such quorum sensing could be based on a slow accumulation of the inducing peptide (the product of the IF gene in FIG. 1) in the early stages of growth as a result of low constitutive production. At a certain point the accumulated peptide then triggers an autoinduction pathway resulting in increased expression of genes encoding the inducing peptide itself (IF, FIG. 1), the bacteriocin and corresponding immunity protein (P, I), the processing and transport machinery for both the bacteriocin and the inducing peptide (T, A), and the two-component system that transduces the induction signal (K, R) (FIG. 5).

It should be noted that the statement that the gene products of IF, K, and R (or analogues thereof from other bacteriocin producing strains, for example from the corresponding system in *Lactobacillus plantarum* C11) are enough to induce transcription of a gene that is preceded by the promoter element depicted in FIG. 4 is under investigation. It is possible that the product of a hitherto unknown gene is also required. In the present invention references to the group IF, K and R (or analogues thereof) should therefore be interpreted as a reference to IF, K, R and such a possible extra gene if it would appear to exist.

It will be understood by those with skill in the art that the inducing mechanism described in the previous examples can be used generally for establishing regulated gene expression in *Lactobacillus sake, Lactobacillus plantarum*, most likely lactobacilli in general and, possibly, other LAB. Those with skill in the art will understand that a long range of applications is conceivable. For example: One could construct a plasmid that contains 1) the K and R genes found in *Lactobacillus sake* LTH673, placed under control of a constitutive promoter, plus 2) a cloned gene encoding a desired enzymatic property under control of the promoter element depicted in FIG. 4. One could then use transformation to introduce this plasmid in a Lactobacillus (or maybe any LAB) strain in which genes under control of the promoter element depicted in FIG. 4 are normally switched off. The desired enzymatic activity encoded by the cloned gene can now be switched on at will, by adding the 19-residue inducing peptide depicted in FIG. 2. Quantities of inducing peptide needed are low and the costs of using this chemically synthesized compound are therefore low.

Those with skill in the art will understand that many variations are conceivable. They concern for example 1) the promoter used to express K and R, 2) the exact promoter used to express the desired enzymatic activity (there are small differences between the promoter elements depicted in FIG. 4), 3) the number of genes involved in the genetic constructions (instead of K and R, one could also use IF, K, and R in a LAB strain that has the ability to cleave of the IF leader peptide; this would give a more autoinducible character to the engineered system) and 4) the genetic methods used (some or all genes involved could be integrated in the chromosome of the host cell instead of being maintained on plasmids). The use of chromosomal integration to establish the regulated expression of a desired enzymatic property in LAB would result in highly stable, fully food grade genetically manipulated bacterial strains.

References

1. Klaenhammer, T. R. 1993. Genetics of bacteriocins produced by lactic acid bacteria. FEMS Microbiol. Rev. 12:39–86.
2. Jack, R. W., J. R. Tagg, and B. Ray. 1995. Bacteriocins of Gram-positive bacteria. Microbiol. Rev. 59:171–200.
3. Håvarstein, L. S., D. B. Diep, and I. F. Nes. 1995. A family of ABC transporters carry out proteolytic processing of their substrates concomitant with export. Mol. Microbiol. 16:229–240.
4. Parkinson, J. S. 1993. Signal transduction schemes in bacteria. Cell 73:857–871.
5. Russo, F. D., and T. J. Silhavy. 1993. The essential tension: opposed reactions in bacterial two-component regulatory systems. Trends Microbiol. 1:306–310.
6. Stock, J. B., A. J. Ninfa, and A. M. Stock. 1989. Protein phosphorylation and regulation of adaptive responses in bacteria. Microbiol. Rev. 53:450–490.
7. Schillinger, U., and F.-K. Lücke. 1989. Antibacterial activity of *Lactobacillus sake* isolated from meat. Appl. Environ. Microbiol. 55:1901–1906.
8. Tichaczek, P. S., J. Nissen-Meyer, I. F. Nes, R. F. Vogel, and W. P. Hammes. 1992. Characterization of the bacteriocins curvacin A from *Lactobacillus curvatus* LTH1174 and sakacin P from *L. sake* LTH673. System. Appl. Microbiol. 15:460–468.
9. Daeschel, M. A., M. C. McKenney, and L. C. McDonald. 1990. Bacteriocidal activity of *Lactobacillus plantarum* C11. Food Microbiol. 7:91–99.
10. Venema, K., J. Kok, J. D. Marugg, M. Y. Toonen, A. M. Ledeboer, G. Venema, and M. L. Chikindas. 1995. Functional analysis of the pediocin operon of *Pediococcus acidilactici* PAC1.0: PedB is the immunity protein and PedD is the precursor processing enzyme. Mol. Microbiol. 17:515–522.
11. Balaban, N., R. P. Novick. 1995. Autocrine regulation of toxin synthesis by *Staphylococcus aureus*. Proc. Natl. Acad. Sci. USA 92:1619–1623.
12. Diep, D. B., L. S. Håvarstein, J. Nissen-Meyer, and I. F. Nes. 1994. The gene encoding plantaricin A, a bacteriocin from *Lactobacillus plantarum* C11, is located on the same transcription unit as an agr-like regulatory system. Appl. Environ. Microbiol. 60:160–166.
13. Higgins, C. F. 1992. ABC transporters: from microorganisms to man. Annu. Rev. Cell Biol. 8:67–113.
14. Fath, M. J., and R. Kolter. 1993. ABC transporters: bacterial exporters. Microbiol. Rev. 57:995–1017.

What is claimed is:

1. An isolated nucleic acid comprising:
   a promoter comprising two repeated nucleotide sequences 5 to 10 nucleotides long and spaced 17 to 23 nucleotides apart, wherein the downstream member of said repeated sequence is located 30 to 38 nucleotides upstream from a −10 region of a bacterial gene,
   wherein said repeated nucleotide sequences are selected from the group consisting of nucleotides 7–14 and 30–38 of SEQ ID NO:6, nucleotides 7–14 and 30–38 of SEQ ID NO:7, nucleotides 7–14 and 30–38 of SEQ ID NO:8, nucleotides 7–14 and 31–38 of SEQ ID NO:9, and nucleotides 7–8, 10–14 and 31–38 of SEQ ID NO:10;
   wherein, when present in a Lactobacillus host cell, said promoter is inducible by a peptide having an amino acid sequence of SEQ ID NO: 1 or of amino acids 19–37 of SEQ ID NO: 3; and
   a polynucleotide of interest obtained from a source other than a Lactobacillus cell, operatively linked to the promoter so that the promoter controls transcription of the polynucleotide of interest.

2. A vector comprising a promoter that, when present in a Lactobacillus host cell, is inducible by a peptide having an amino acid sequence of SEQ ID NO: 1 or of amino acids 19–37 of SEQ ID NO: 3 and that comprises two repeated nucleotide spaced 17 to 23 nucleotides apart and selected from the group consisting of nucleotides 7–14 and 30–38 of SEQ ID NO:6, nucleotides 7–14 and 30–38 of SEQ ID NO:7, nucleotides 7–14 and 30–38 of SEQ ID NO:8, nucleotides 7–14 and 31–38 of SEQ ID NO:9, and nucleotides 7–8, 10–14 and 31–38 of SEQ ID NO:10;
   the promoter being operatively linked to a multiple cloning site for inserting a polynucleotide of interest so that the inducible promoter controls transcription of an inserted polynucleotide of interest.

3. The vector of claim 2, further comprising a polynucleotide of interest that encodes a polypeptide having proteolytic activity, carbohydrolytic activity or autolytic activity.

4. A gene expression system comprising the vector of claim 2 and further comprising a Lactobacillus host cell.

5. A kit comprising:
   (a) the vector of claim 2; and
   (b) a peptide consisting of an amino acid sequence of SEQ ID NO: 1 or amino acids 19–37 of SEQ ID NO: 3.

6. The kit of claim 5 further comprising a Lactobacillus host cell.

7. A vector comprising a promoter that, when present in a Lactobacillus host cell, is inducible by a peptide having an amino acid sequence of SEQ ID NO: 1 or of amino acids 19–37 of SEQ ID NO: 3 and that comprises two repeated nucleotides spaced 17 to 23 nucleotides apart and selected from the group consisting of nucleotides 7–14 and 30–38 of SEQ ID NO:6, nucleotides 7–14 and 30–38 of SEQ ID NO:7, nucleotides 7–14 and 30–38 of SEQ ID NO:8, nucleotides 7–14 and 31–38 of SEQ ID NO:9, and nucleotides 7–8, 10–14 and 31–38 of SEQ ID NO:10;
   operatively linked to a polynucleotide of interest that encodes an enzyme having proteolytic activity, carbohydrolytic activity or autolytic activity so that the inducible promoter controls transcription of the polynucleotide of interest.

8. A vector comprising a promoter that, when present in a Lactobacillus host cell, is inducible by a peptide having an amino acid sequence of SEQ ID NO: 1 or of amino acids 19–37 of SEQ ID NO: 3 and that comprises two repeated nucleotide spaced 17 to 23 nucleotides apart and selected from the group consisting of nucleotides 7–14 and 30–38 of SEQ ID NO:6, nucleotides 7–14 and 30–38 of SEQ ID NO:7, nucleotides 7–14 and 30–38 of SEQ ID NO:8, nucleotides 7–14 and 31–38 of SEQ ID NO:9, and nucleotides 7–8, 10–14 and 31–38 of SEQ ID NO:10;

operatively linked to a restriction enzyme site for inserting a polynucleotide of interest so that the inducible promoter controls transcription of an inserted polynucleotide of interest.

9. A kit comprising:

(a) the vector of claim 8; and (b) a peptide consisting of an amino acid sequence of SEQ ID NO: 1 or amino acids 19–37 of SEQ ID NO: 3.

10. The kit of claim 9, further comprising a Lactobacillus host cell.

11. A vector comprising a promoter that, when present in a Lactobacillus host cell, is inducible by a peptide having an amino acid sequence of SEQ ID NO: 1 or of amino acids 19–37 of SEQ ID NO: 3 and that comprises two repeated nucleotide spaced 17 to 23 nucleotides apart and selected from the group consisting of nucleotides 7–14 and 30–38 of SEQ ID NO:6, nucleotides 7–14 and 30–38 of SEQ ID NO:7, nucleotides 7–14 and 30–38 of SEQ ID NO:8, nucleotides 7–14 and 31–38 of SEQ ID NO:9, and nucleotides 7–8, 10–14 and 31–38 of SEQ ID NO:10;

operatively linked to a polynucleotide of interest obtained from a source other than a Lactobacillus cell, so that the inducible promoter controls transcription of an inserted polynucleotide of interest.

12. A kit comprising:

(a) the vector of claim 11; and (b) a peptide consisting of an amino acid sequence of SEQ ID NO: 1 or amino acids 19–37 of SEQ ID NO: 3.

13. The kit of claim 12, further comprising a Lactobacillus host cell.

14. A host cell comprising the vector of claim 2.

15. A host cell comprising the vector of claim 3.

16. A host cell comprising the vector of claim 7.

17. A host cell comprising the vector of claim 8.

18. A host cell comprising the vector of claim 11.

19. The host cell of claim 14 that is a cell of a lactic acid bacterium.

20. The host cell of claim 15 that is a cell of a lactic acid bacterium.

21. The host cell of claim 16 that is a cell of a lactic acid bacterium.

22. The host cell of claim 17 that is a cell of a lactic acid bacterium.

23. The host cell of claim 18 that is a cell of a lactic acid bacterium.

24. The host cell of claim 14 that is a cell of a Lactobacillus cell.

25. The host cell of claim 15 that is a Lactobacillus cell.

26. The host cell of claim 16 that is a Lactobacillus cell.

27. The host cell of claim 17 that is a Lactobacillus cell.

28. The host cell of claim 18 that is a Lactobacillus cell.

* * * * *

SEQUENCE LISTING

<160> NUMBER OF SEQ ID NOS: 12

<210> SEQ ID NO 1
<211> LENGTH: 26
<212> TYPE: PRT
<213> ORGANISM: Lactobacillus plantarum

<400> SEQUENCE: 1

Lys Ser Ser Ala Tyr Ser Leu Gln Met Gly Ala Thr Ala Ile Lys Gln
1               5                   10                  15

Val Lys Lys Leu Phe Lys Lys Trp Gly Trp
            20                  25

<210> SEQ ID NO 2
<211> LENGTH: 114
<212> TYPE: DNA
<213> ORGANISM: Lactobacillus sake
<220> FEATURE:
<221> NAME/KEY: CDS
<222> LOCATION: (1)..(114)
<223> OTHER INFORMATION:

<400> SEQUENCE: 2 atg atg ata ttt aaa aaa ctt tca gaa aaa gaa ttg caa aaa ata aac        48
Met Met Ile Phe Lys Lys Leu Ser Glu Lys Glu Leu Gln Lys Ile Asn
1               5                   10                  15 ggt ggt atg gca gga aat agt tct aat ttt att cat aag att aaa caa        96
Gly Gly Met Ala Gly Asn Ser Ser Asn Phe Ile His Lys Ile Lys Gln
            20                  25                  30 att ttt acc cat cgt taa                                               114
Ile Phe Thr His Arg
        35

<210> SEQ ID NO 3
<211> LENGTH: 37
<212> TYPE: PRT
<213> ORGANISM: Lactobacillus sake

<400> SEQUENCE: 3

Met Met Ile Phe Lys Lys Leu Ser Glu Lys Glu Leu Gln Lys Ile Asn
1               5                   10                  15

Gly Gly Met Ala Gly Asn Ser Ser Asn Phe Ile His Lys Ile Lys Gln
            20                  25                  30

Ile Phe Thr His Arg
        35

<210> SEQ ID NO 4
<211> LENGTH: 186
<212> TYPE: DNA
<213> ORGANISM: Lactobacillus sake
<220> FEATURE:
<221> NAME/KEY: CDS
<222> LOCATION: (1)..(186)
<223> OTHER INFORMATION:

<400> SEQUENCE: 4 atg gaa aag ttt att gaa tta tct tta aaa gaa gta aca gca att aca        48
Met Glu Lys Phe Ile Glu Leu Ser Leu Lys Glu Val Thr Ala Ile Thr
1               5                   10                  15 ggt gga aaa tat tat ggt aac ggt gta cac tgt gga aaa cat tca tgt        96
Gly Gly Lys Tyr Tyr Gly Asn Gly Val His Cys Gly Lys His Ser Cys
            20                  25                  30

```
acc gta gac tgg gga aca gct att gga aat atc gga aat aat gca gct    144
Thr Val Asp Trp Gly Thr Ala Ile Gly Asn Ile Gly Asn Asn Ala Ala
         35                  40                  45 gca aac tgg gcc aca ggc gga aac gct ggc tgg aat aaa taa            186
Ala Asn Trp Ala Thr Gly Gly Asn Ala Gly Trp Asn Lys
 50                  55                  60
```

<210> SEQ ID NO 5
<211> LENGTH: 61
<212> TYPE: PRT
<213> ORGANISM: Lactobacillus sake

<400> SEQUENCE: 5

```
Met Glu Lys Phe Ile Glu Leu Ser Leu Lys Glu Val Thr Ala Ile Thr
 1               5                  10                  15

Gly Gly Lys Tyr Tyr Gly Asn Gly Val His Cys Gly Lys His Ser Cys
             20                  25                  30

Thr Val Asp Trp Gly Thr Ala Ile Gly Asn Ile Gly Asn Asn Ala Ala
         35                  40                  45

Ala Asn Trp Ala Thr Gly Gly Asn Ala Gly Trp Asn Lys
 50                  55                  60
```

<210> SEQ ID NO 6
<211> LENGTH: 81
<212> TYPE: DNA
<213> ORGANISM: Lactobacillus sake

<400> SEQUENCE: 6
gagttcttaa cgttaatccg aaaaaaacta acgttaatat taaaaataa gatccgcttg    60 tgaattatgt ataatttgat t                                            81

<210> SEQ ID NO 7
<211> LENGTH: 80
<212> TYPE: DNA
<213> ORGANISM: Lactobacillus sake

<400> SEQUENCE: 7
cgcatattaa cgtttaaccg ataaagttga acgttaatat ttttttttgcg cagaaatggt    60 aaattgaagc ataatagtct                                              80

<210> SEQ ID NO 8
<211> LENGTH: 81
<212> TYPE: DNA
<213> ORGANISM: Lactobacillus sake

<400> SEQUENCE: 8
gcagcattaa cgttaatttt gataaacgta acgttaatgg ataatcatcc tgtttacaaa    60
tagtgtatga cataattaag t                                            81

<210> SEQ ID NO 9
<211> LENGTH: 81
<212> TYPE: DNA
<213> ORGANISM: Lactobacillus sake

<400> SEQUENCE: 9
ttgatattag cgtttaacag ttaaattaat acgttaataa ttttttttgtc tttaaatagg    60 gatttgaagc ataatggtgt t                                            81

<210> SEQ ID NO 10
<211> LENGTH: 81

-continued

```
<212> TYPE: DNA
<213> ORGANISM: Lactobacillus plantarum

<400> SEQUENCE: 10
tggtgattca cgtttaaatt taaaaaatgt acgttaatag aaataattcc tccgtacttc    60
aaaaacacat tatcctaaaa g                                              81

<210> SEQ ID NO 11
<211> LENGTH: 80
<212> TYPE: DNA
<213> ORGANISM: Staphylococcus aureus

<400> SEQUENCE: 11
tacatttaac agttaagtat ttatttccta cagttaggca atataatgat aaaagattgt    60
actaaatcgt ataatgacag                                                80

<210> SEQ ID NO 12
<211> LENGTH: 80
<212> TYPE: DNA
<213> ORGANISM: Staphylococcus aureus

<400> SEQUENCE: 12
aaaaatttac agttaagaat aaaaaacgac tagttaagaa aaattggaaa aataaatgct    60
tttagcatgt ttaatataac                                                80
```